United States Patent [19]

Lalancette

[11] 3,950,262

[45] Apr. 13, 1976

[54] GRAPHITE INTERCALATED ANTIMONY PENTAFLUORIDE

[75] Inventor: Jean-Marc Lalancette, Sherbrooke, Canada

[73] Assignee: Ventron Corporation, Beverly, Mass.

[22] Filed: Nov. 26, 1973

[21] Appl. No.: 419,097

[52] U.S. Cl............ 252/187 R; 252/441; 252/447; 423/489
[51] Int. Cl.$^2$. B01J 27/12; B01J 23/18; B01J 37/02
[58] Field of Search............... 252/187 R, 441, 447; 423/489

[56] References Cited
UNITED STATES PATENTS

| | | | |
|---|---|---|---|
| 3,678,120 | 7/1972 | Bloch | 252/441 |
| 3,835,067 | 9/1974 | Schneider | 252/447 |
| 3,840,566 | 12/1974 | Lalancette | 252/447 |

*Primary Examiner*—Benjamin R. Padgett
*Assistant Examiner*—Irwin Gluck
*Attorney, Agent, or Firm*—Cushman, Darby & Cushman

[57] ABSTRACT

A new graphite intercalated antimony pentafluoride wherein the antimony pentafluoride is present up to 75% by weight. This compound is obtained as a black, free-flowing powder which is substantially resistant to hydrolysis under conditions which normally hydrolyze antimony pentafluoride. The graphite intercalated antimony pentafluoride is particularly useful for exchange reactions in the preparation of organic fluorides.

4 Claims, No Drawings

GRAPHITE INTERCALATED ANTIMONY PENTAFLUORIDE

The present invention relates to the preparation of antimony pentafluoride intercalated in the lattices of graphite to provide a novel compound suitable for exchange reactions in the preparation of organic fluorides.

BACKGROUND OF THE INVENTION

Fluorinated hydrocarbons also called fluorocarbons are finding more and more industrial uses. For example, amongst the well known fluorocarbons then are those known commercially as Freon, Teflon, Kel-F and fluorothene. The unique physical properties of the various polymers containing fluorine have resulted in their use both as solid materials and as liquids for lubricants. Generally fluorocarbons are prepared by either the metallic fluoride process or the direct fluorination process.

In order to appreciate the problem implied in the preparation of organic fluorides, it should be noted that the amount of energy liberated when fluorine reacts with a hydrocarbon is greater than the energy necessary to dissociate a carbon-carbon bond. From this it results that the uncontrolled reaction of fluorine with organic molecules is explosive and thus the only product generally identifiable is carbon tetrafluoride. One method of moderating the reaction is to use a less reactive fluorinating agent than fluorine itself. Certain metallic fluorides such as $CoF_3$, $AgF$, $CeF_4$ and $MnF_4$ have been found suitable for this purpose with cobaltic fluoride being preferred.

Unfortunately, even with the milder metallic fluoride intermediate the preparation of fluorocarbons of high molecular weight, which are of interest as lubricating oils, remains difficult to prepare because of the still very high reactivity of the metallic fluorides.

Another method for preparing fluorocarbons is to carry out an exchange reaction between organic halides and inorganic fluorides. For this type of exchange antimony pentafluoride is usually used. However, the use of antimony pentafluoride or other fluorides is not without drawbacks, since these materials are very hygroscopic and very difficult to handle safely.

Accordingly, since antimony pentafluoride is useful as a catalyst or as a source of fluorine in fluorination reactions, it would be highly desirable to provide an antimony pentafluoride in a form where it can be handled easily and used either as a catalyst or a source of fluorine, while being stable to conditions which generally cause antimony pentafluoride to undergo hydrolysis.

THE INVENTION

In accordance with the present invention there is now provided an antimony pentafluoride which is intercalated in graphite and which in this form overcomes the prior art disadvantages of antimony pentafluoride when not intercalated. The antimony pentafluoride obtained in accordance with the present invention is substantially stable at room temperature and provides substantially greater resistance to hydrolysis than normal antimony pentafluoride.

The new graphite intercalated antimony pentafluoride is a non sticky, free-flowing black glossy powder and can contain up to 75% by weight of antimony pentafluoride. As an example of the stability of the graphite intercalated antimony pentafluoride a sample containing 35% by weight of antimony pentafluoride was exposed to moist air for a period of 15 minutes without decomposition, while under similar conditions antimony pentafluoride reacts very rapidly giving off heavy fumes of antimony oxide and hydrofluoric acid. Another sample of graphite intercalated antimony pentafluoride containing 5% by weight of antimony pentafluoride gave a detectable amount of hydrogen fluoride after only 50 minutes of exposure to moist air. It has also been found that graphite intercalated antimony pentafluoride is a milder agent for exchange of halogen with an organic chloride, thus making the graphite intercalated antimony pentafluoride surprisingly useful as a fluorination agent in terms of control of the reaction and simplification of the handling of the fluorating agent.

Though the intercalation of metals and metal salts in the lattice of graphite is known in the art, the salts which have been easily intercalated have been the chlorides of transition metals such as ferric chloride or cobaltic chloride, there has been very few intercalation of fluoride salts to a point that certain authors report that the fluorides of transition metal are not intercalated by standard techniques (P. Pascal, Nouveau Traité de Chimie Minérale, 1968, vol, VIII, 402, Masson et Cie Paris).

Also in accordance with the present invention, and contrary to the references found in the chemical literature it has been found that intercalation of antimony pentafluoride in the lattice graphite can be easily achieved by heating a mixture of antimony pentafluoride and graphite at a temperature range of from 40° to 150°C, with a temperature of 110°C. being preferred, with a duration of a contact of a few days. The differential thermal analysis and the X-ray diffraction show clearly that the fluoride is intercalated in the lattice. The thermal analysis produces a sharp inflexion at 492° and the X-ray pattern is typical of an expanded lattice, the strong band for pure graphite at 3.35A being almost completely eliminated by the intercalation and a new band appearing at 11.10A.

As can be appreciated by those skilled in the art this is a most simple procedure in comparison with the techniques required for the intercalation of other antimony halides such as antimony pentachloride. The intercalation of chlorides is carried out by introducing the antimony pentachloride and graphite in an atmosphere of helium in an aluminum autoclave. The system is then flushed with chlorine and after a suitable pressure has built in the system, it is closed and the autoclave is heated at 260°C. for 24 hours. The non-intercalated antimony pentachloride is removed by breaking the solid mass in a dry atmosphere and heating under vacuum at about 290°C.

The elementary analysis performed on the intercalates of antimony pentafluoride of the present invention indicate a ratio of 5 to 1 for fluorine and antimony. This shows that the antimony pentafluoride is intercalated and that there is no appreciable reaction of antimony pentafluoride with Pyrex flasks to give antimony trifluoride and the volatile silicon tetrafluoride. It is also observed that after the intercalation reaction no antimony salt can be extracted from the intercalate, even with aqua regia. After degradation by sulfuric acid of the lattice of graphite it was then possible to recover the antimony pentafluoride as antimony oxide and hydrofluoric acid.

The present invention will be more fully understood by referring to the following examples.

EXAMPLE 1

Graphite, prior to its use for the intercalation is thoroughly dried by heating under vacuum at 150°C. for a period of at least 24 hours. 5.0 g of dry graphite are mixed with 5.0 g of antimony pentafluoride in a 100 ml pyrex flask, the flask is then closed with a Teflon stopper, evacuated, and heated in an oven for 48 hours. After cooling, the material thus obtained is a 50% intercalate of $SbF_5$ in graphite. The material appears as a black, free-flowing powder. The antimony was determined by the method of Zeiss (Anal. Abst., 18, 2349 (1970) after a digestion of the graphite in sulfuric acid. Fluorine was determined as HF. (A.I. vogel, Quantitative Inorganic Analysis, 3rd Ed. p. 570, 1961).

The whole operation is carried out under a dry nitrogen atmosphere in a dry box.

By proceeding in the same manner and using the appropriate amounts of graphite and antimony pentafluoride, there is obtained a graphite intercalated antimony pentafluoride containing 8,10,20,30,50 and 75% of antimony pentafluoride by weight, the intercalation being essentially quatitative, up to 75% of $SbF_5$.

EXAMPLE 2

To illustrate the facility which the graphite intercalated antimony pentafluoride can be used as a fluorinating agent the following reaction was carried out.

A mixture of chlorobenzene (0.05 mole) and graphite intercalated antimony pentafluoride (0.02 mole) containing 35% by weight of antimony pentafluoride were placed in a sealed tube and heated at 17°C. for 1 hour. After cooling the reaction mixture was extracted with pentane, washed with 3% sodium carbonate and dried. After evaporation of the solvent, the reaction product was identified as fluorobenzene by vapor phase chromatography and its infra-red spectrum. The yield was 35% and essentially all of the unreacted chlorobenzene was recovered.

Carrying out the same reaction by substituting pure antimony pentafluoride for the graphite intercalated antimony pentafluoride gives essentially a black tar.

EXAMPLE 3

In order to evaluate the resistance to moisture, a 0.5 g sample was placed at the center of a watch glass 8cm in diameter and covered by an inverted watch glass of the same diameter. A wet Congo paper strip was then placed between the two watch glasses, alongside the rim, and the time required for the detection of hydrofluoric acid from hydrolysis was measured. With pure $SbF_5$, the reaction was almost instantaneous and with a 5% intercalate, 50 minutes were required for the appearance of HF. In the case of a 40% intercalate prepared according to Example 1 the acid reaction appeared after 10 minutes.

We claim:

1. A composition consisting essentially of graphite intercalated antimony pentafluoride.

2. A composition according to claim 1 wherein the amount of antimony pentafluoride is 5 to 75% by weight.

3. As a new composition, graphite intercalated antimony pentafluoride containing up to 75% by weight of antimony pentafluoride, the intercalate being in the form of a black, free-flowing powder which is substantially resistant to moisture.

4. A process for preparing a graphite intercalated antimony pentafluoride which comprises heating antimony pentafluoride and graphite in a sealed evacuated container at a temperature of from 40° to 150°C. for 1 to 48 hrs. and recovering the graphite intercalated antimony pentafluoride.

* * * * *